United States Patent
Li et al.

(10) Patent No.: US 6,579,730 B2
(45) Date of Patent: Jun. 17, 2003

(54) MONITORING PROCESS FOR OXIDE REMOVAL

(75) Inventors: Haojiang Li, Saratoga, CA (US); Peijun Ding, San Jose, CA (US); Suraj Rengarajan, San Jose, CA (US)

(73) Assignee: Applied Materials, Inc., Santa Clara, CA (US)

(*) Notice: Subject to any disclaimer, the term of this patent is extended or adjusted under 35 U.S.C. 154(b) by 0 days.

(21) Appl. No.: 09/908,829

(22) Filed: Jul. 18, 2001

(65) Prior Publication Data

US 2003/0017628 A1 Jan. 23, 2003

(51) Int. Cl.[7] .......................... H01L 31/26; H01L 21/66
(52) U.S. Cl. ......................... 438/14; 438/934
(58) Field of Search .............................. 438/14, 17, 18, 438/905, 934, 762

(56) References Cited

U.S. PATENT DOCUMENTS

| | | | |
|---|---|---|---|
| 3,650,020 A | 3/1972 | Mar | 29/574 |
| 3,660,250 A | 5/1972 | Duffy et al. | 204/1 T |
| 4,868,490 A | 9/1989 | Blumenthal | 324/64 |
| 5,635,338 A | * 6/1997 | Joshi et al. | |
| 5,698,989 A | * 12/1997 | Nulman | |
| 5,728,629 A | * 3/1998 | Mizuno et al. | |
| 6,107,192 A | 8/2000 | Subrahmanyan et al. | 438/637 |
| 6,486,082 B1 | * 11/2002 | Cho et al. | |

FOREIGN PATENT DOCUMENTS

GB 2 281 402 A 3/1995 ........... G01R/31/26

OTHER PUBLICATIONS

Cohen, et al. "Reduction of Metal Oxide in a Dual Frequency Etch Chamber", U.S. patent application Ser. No. 09/082,746, filed May 21, 1998.
PCT International Search Report for PCT/US02/21505 dated Nov. 26, 2002.
Equipment Frontiers "Surface resistance analysis: A new thin–film characterization tool" by Jon S. Martens, et al., Dec. 1994, Solid State Technology, Measurements, pp. 51–54.

* cited by examiner

*Primary Examiner*—David Nelms
*Assistant Examiner*—Phuc T. Dang
(74) *Attorney, Agent, or Firm*—Moser, Patterson & Sheridan LLP

(57) ABSTRACT

Generally, a method for monitoring a process of removing native oxides from an at least partially exposed layer disposed on a substrate is provided. In one embodiment, a method for monitoring includes disposing the substrate in a process chamber, exposing the at least partially exposed layer to a reactive pre-clean process, removing the substrate from the process chamber and measuring a sheet resistance of the exposed layer. In another embodiment, a method includes disposing the substrate in a process chamber, exposing the at least partially exposed conductive layer to a reactive pre-clean process that comprises an oxide reduction step, removing the substrate from the process chamber, contacting the conductive layer with one or more contact members, measuring a sheet resistance of the exposed conductive layer between the contact members, and comparing the measured resistance to a known value.

31 Claims, 6 Drawing Sheets

MONITORING PROCESS FOR OXIDE REMOVAL

BACKGROUND OF THE INVENTION

1. Field of the Invention

Embodiments of the invention generally relate to a method for monitoring a process for pre-cleaning an at least partially exposed layer disposed on a substrate.

2. Background of the Related Art

Sub-quarter micron, multi-level metallization is one of the key technologies for the next generation of ultra large scale integration (ULSI). The multilevel interconnects that lie at the heart of this technology require planarization of interconnect features formed in high aspect ratio apertures, including contacts, vias, lines and other features. Reliable formation of these interconnect features is very important to the success of ULSI and to the continued effort to increase circuit density and quality on individual substrates and die.

The increase in circuit densities primarily results from a decrease in the widths of vias, contacts and other features as well as a decrease in the thickness of dielectric materials between these features. Cleaning of the features to remove contaminants prior to metallization is required to improve device integrity and performance. The decrease in width of the features results in larger aspect ratios for the features and increased difficulty in cleaning the features prior to filling the features with metal or other materials. Failure to clean the features can result in void formation within the features or an increase in the resistance of the features. Therefore, there is a great amount of ongoing effort being directed at cleaning small features having high aspect ratios, especially where the ratio of feature width to height is 3:1 or larger.

The presence of native oxides and other contaminants within a small feature contributes to void formation by promoting uneven distribution of a depositing material such as metal. Regions of increased growth merge and seal the small features before regions of limited growth can be filled with the depositing metal. Native oxides form within the features when a portion of a layer (or sublayer), such as silicon, aluminum, or copper, is exposed to oxygen in the atmosphere or is damaged during a plasma etch step. Other contaminants within the features can be sputtered material from an oxide over-etch, residual photoresist from a stripping process, leftover polymer from a previous oxide etch step, or redeposited material from a sputter etch process.

The presence of native oxides and other contaminants also can reduce the electromigration resistance of vias and small features. The contaminants can diffuse into the dielectric layer, the sublayer, or the deposited metal and alter the performance of devices that include the small features. Although contamination may be limited to a thin boundary region within the features, the thin boundary region is a substantial part of the small features. The acceptable level of contaminants in the features decreases as the features get smaller in width.

Pre-cleaning of features to remove native oxides and other contaminants has become increasingly utilized to prepare surfaces for barrier layer or metal deposition. One process for removing native oxides and other contaminants from polysilicon, copper and metal surfaces is described in U.S. Pat. No. 6,107,192, issued Aug. 22, 2000 to Subrahmanyan et al., which is hereby incorporated by reference in its entirety. This process, which may be performed in a REACTIVE PRE-CLEAN™ II process chamber, available from Applied Materials, Inc., of Santa Clara, Calif., generally includes a first cleaning step and a second reducing step. The cleaning step features a soft plasma etch using a reactive gas such as oxygen, a mixture of $CF_4/O_2$, or a mixture of $He/NF_3$, wherein the plasma is preferably introduced to the chamber from a remote plasma source. The remaining native oxides are then reduced in the second step by treatment with a hydrogen comprising plasma.

Typically following the first or both pre-cleaning steps, the features can be filled with metal by available metallization techniques which typically include depositing a barrier/liner layer on exposed dielectric surfaces prior to deposition of aluminum, copper, or tungsten. The pre-cleaning and metallization steps can be conducted remotely or preferably on integrated processing platforms, such as the family of ENDURA®, PRODUCER® and CENTURA® processing platforms, all available from Applied Materials, Inc., of Santa Clara, Calif.

As the removal of native oxide and other contaminants directly enhance device performance, monitoring of the effectiveness of the pre-clean process is advantageous to ensure robust process chamber performance. Typically, pre-clean processes are monitored by taking reflectivity measurements of the exposed layer on the substrate. As the presence of oxides and other contaminants on the oxide layer directly changes the reflectivity of the exposed layer, the measured reflectivity is an indicator of the presence of native oxides or other contaminants on the exposed surface of the substrate. Reflectivity is typically measured in pre-clean processes using optical devices. Generally, a beam of light is reflected off the substrate surface to the sensor. As the reflectivity of the exposed film is indicative of the composition of the film (i.e., whether contaminants or native oxides are residing on the surface) the cleanliness of the film can be determined.

However, when using optical devices to measure reflectivity of a material, care must be taken not to introduce measurement errors. For example, focal distance between the sensors and the substrate, which are easily disturbed, must be maintained. This results in a need to frequently calibrate the measurement system. Additionally, the beam generator and sensor are sensitive to contamination on their lenses. Moreover, the surface roughness of the film, which could be changed by the pre-clean process, may affect the reflectivity by changing the refraction characteristics of the surface. Thus, as the demand for smaller feature sizes increases the importance of the elimination of contaminants and native oxides from the exposed surfaces, a more robust measuring system is needed to ensure robust and efficient pre-cleaning processes.

Therefore, there is a need for an improved method for pre-cleaning an at least partially exposed layer disposed on a substrate.

SUMMARY OF THE INVENTION

In one aspect of the invention, a method for monitoring a process of removing native oxides from an at least partially exposed layer disposed on a substrate is provided. In one embodiment, a method for monitoring a process of removing native oxides from an at least partially exposed layer disposed on a substrate includes disposing the substrate in a process chamber, exposing the at least partially exposed layer to a reactive pre-clean process and measuring a sheet resistance of the exposed layer.

In another embodiment, a method for monitoring a process of removing native oxides from an at least partially exposed conductive layer disposed on a substrate includes disposing the substrate in a process chamber, exposing the at least partially exposed conductive layer to a reactive pre-clean process that comprises an oxide reduction step, removing the substrate from the process chamber, contacting the at least partially conductive layer with one or more contact members, measuring a sheet resistance of the at least partially exposed conductive layer between the contact members, and comparing the measured resistance to a known value.

In yet another embodiment of the invention, a method for monitoring a process of removing native oxides from an at least partially exposed conductive layer disposed on a substrate includes depositing a copper seed layer on a sample substrate in a first chamber, exposing the copper seed layer to a reactive pre-clean process in a second chamber to remove native oxides from the copper seed layer, transferring the sample substrate from the second chamber to a metrology device, measuring the sheet resistance of the conductive layer, and comparing the measured sheet resistance to a known value.

BRIEF DESCRIPTION OF THE DRAWINGS

So that the manner in which the above-recited features, advantages and objects of the present invention are attained can be understood in detail, a more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

To facilitate understanding, identical reference numerals have been used, wherever possible, to designate identical elements that are common to the figures.

DETAILED DESCRIPTION OF THE PREFERRED EMBODIMENT

Figure 1:
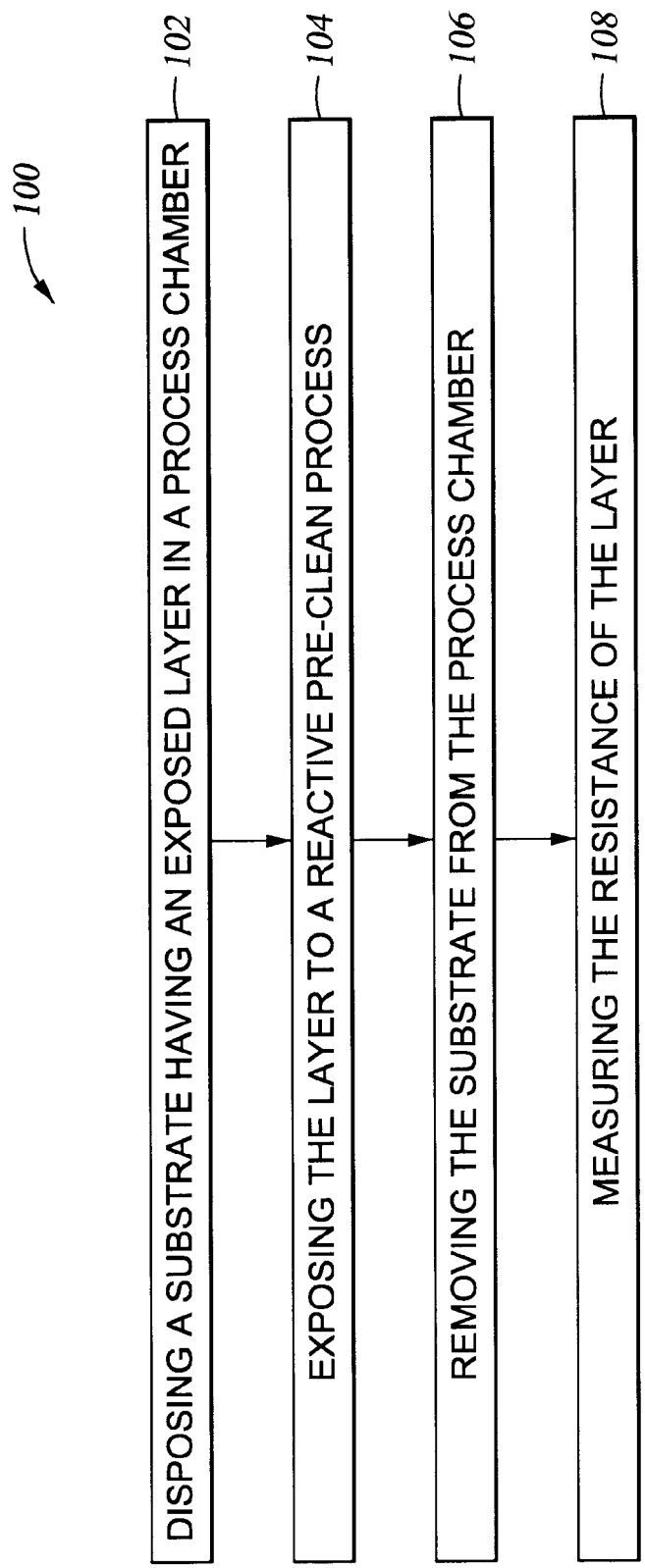
FIG. 1 depicts a flow diagram of one embodiment of a method for monitoring a process for removal of oxides from an exposed layer disposed on a substrate.

Generally, a method for monitoring a process for removal of native oxides from an exposed layer disposed on a substrate is provided. FIG. 1 depicts a flow diagram of one embodiment of a method 100 for monitoring a process for removal of native oxides from an exposed layer disposed on a substrate that includes a step 102 of disposing a substrate having an exposed layer in a process chamber, a step 104 of exposing the layer to a reactive pre-clean process, a step 106 of removing the substrate from the process chamber, and a step 108 of measuring the resistance of the layer. Although the preferred embodiment of the method 100 is described below with reference to an illustrative process chamber performing one embodiment of a pre-clean process to remove native oxides from an exposed copper layer, the inventive monitoring method may be effectively applied in other chambers and while using other processes on other types of exposed materials (ie., other conductors and semiconductors). Generally, the inventive method may be practiced with production substrates through a sampling regime. Alternatively, utility substrates, prepared with an native oxide grown over an exposed material of interest, may be periodically sampled during processing of production substrates.

Figure 2:
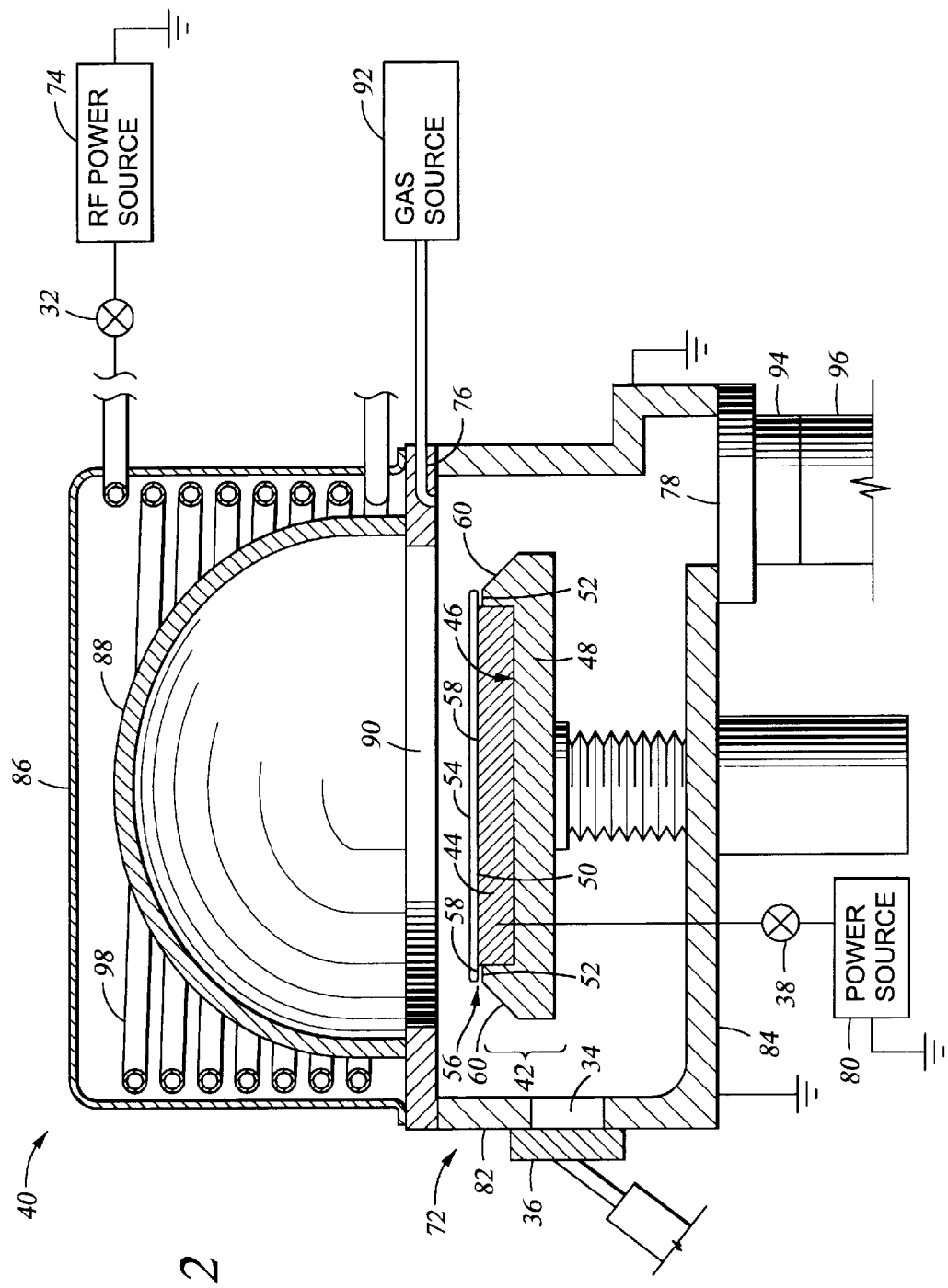
FIG. 2 is sectional view of one embodiment of a pre-clean chamber.

FIG. 2 depicts a cross sectional view of one embodiment of a chamber 40 in which steps 102, 104 and 106 may be practiced. The chamber 40 is preferably a dual frequency etch chamber such as the Pre-Clean II Chamber available from Applied Materials, Inc., of Santa Clara, Calif. Generally, the chamber 40 comprises an enclosure 72, a substrate support 42 disposed within a processing region of the chamber 40, an RF power source 74 connected to an inductive coil 98 disposed outside the enclosure 72 and a power source 80 connected to the substrate support 42 through a mating circuit 38.

The enclosure 72 includes side walls 82, a bottom 84 and a top 86. An access port 34 is generally disposed in the side walls 82 to allow entry and egress of the substrate 54 from the chamber 40. The port 34 is selectively sealed by a slit valve 36 to isolate the process region 90 during processing. One slit valve that may be used to advantage is described in U.S. Pat. No. 5,226,632, issued Jul. 13, 1993 to Tepman, et al., which is hereby incorporated by reference in its entirety. A substrate handling robot utilized to pass the substrate through the port 34 and place the substrate on the substrate support 42 are generally known and have been omitted for the sake of clarity.

A quartz dome 88 is disposed under the top 86 and above the processing region 90. The quartz dome 88 is typically part of a "process kit" that is replaced after a certain number of substrates have been processed in the chamber 40. The inductor coil 98 is generally disposed around the quartz dome 88 and connected through a matching circuit 32 to the RF power source 74. The RF power source 74 inductively couples power to a plasma formed within a processing region 90 during processing. The coil 98 may be vertically stacked about the dome 88 as shown in FIG. 1, disposed equidistant from the dome or disposed in other configurations.

A processing gas supply 92 is coupled to a gas inlet 76 disposed in the chamber 40 and introduces the process and/or other gas(es) into the process region 90 of chamber 40 during processing. A gas exhaust 78 in fluid communication with the process region 90 evacuates the chamber 40 prior to processing. A throttle valve 94 and a vacuum pump 96 coupled to the exhaust port maintain a predetermined pressure within the process region 90 of the chamber 40 during processing.

The substrate support 42 generally comprises a pedestal 44 disposed within a recess 46 on a top surface 50 of a quartz insulator plate 48. The top surface 50 of the pedestal 44 extends slightly higher than the upper annular surface 52 of the quartz insulator plate 48 and is in contact with a central portion of the bottom surface or backside 58 of the substrate 54. The pedestal 44 is connected to the power source 80 that electrically biases the pedestal 44 during processing. The peripheral portion of the substrate 54 extends above the upper annular surface 52 of the quartz insulator plate 48 and forms a gap 56 between the bottom surface 58 of the substrate 54 and the upper annular surface 52 of the quartz insulator plate 48. Optionally, the substrate support 42 includes a temperature controller or a heater (not shown) to control the temperature of the substrate during processing.

In one mode of operation, the substrate 54 having an at least partially exposed metal layer (see the copper layer 304 of FIG. 3) is passed through the port 34 and positioned on the substrate support 42 at step 102. The slit valve 36 is closed and the processing region 90 of the chamber 40 is evacuated.

At step 104, a processing gas comprising a reactive gas that is often combined with an inert gas is introduced through the gas inlet 76 into the processing region 90. Examples of inert gases that may be utilized include helium, argon, nitrogen and other non-reactive gases. Typically, the reactive gases include hydrogen, particularly for processing copper, however, other gases may be utilized including oxygen and fluoride comprising gases. In one embodiment, the processing gas includes helium mixed with about 5 percent or less hydrogen. Typically, the processing gas is flowed into the chamber at between about 10 sccm and about 1000 sccm, and preferably, at about 100 sccm.

To activate the reaction, a plasma is formed from the processing gas in the processing region 90 through inductive coupling and/or capacitive coupling. The initial plasma is preferably struck by biasing the substrate support 42 between about 1 W and about 100 W and between about 100 KHz and about 100 MHz for about 3 seconds. Alternatively, the initial plasma is generated by applying power to the inductive coil 98 or by other ignition methods or devices.

During the reduction reaction period, the inductive coil 98 is biased between about 1 W and about 1000 W at between about 100 KHz and about 60 MHz while the substrate support 42 is biased between about 0 W and about 100 W. Alternatively, during the reduction reaction period, the plasma in the processing region 90 is sustained solely by the inductive coil 98. Alternatively, the plasma within the processing region 90 may be excited and sustained during processing by inductive coupling only, capacitive coupling only or combinations of both inductive and capacitive coupling.

During processing, the chamber pressure is preferably maintained between about 20 mTorr and about 100 mTorr by controlling the open/closed state of the throttle valve 94. A number of operating parameters are adjusted to eliminate sputtering of the copper native oxides by the ions in the plasma and to maximize the reduction reaction. These operating parameters include the power supplied to the inductive coil and the substrate support, the hydrogen concentration and flow rate of the processing gas, the pressure within the processing region 90, and the density of the resulting plasma. Optionally, the temperature of the substrate 54 during processing is controlled by a temperature control device (not shown) within the substrate support 42 to enhance or to activate the reduction reaction for some metal native oxides. However, for the reduction reaction of copper native oxide, it is not necessary to heat (or cool) the substrate 54 to a particular temperature.

Figure 3:
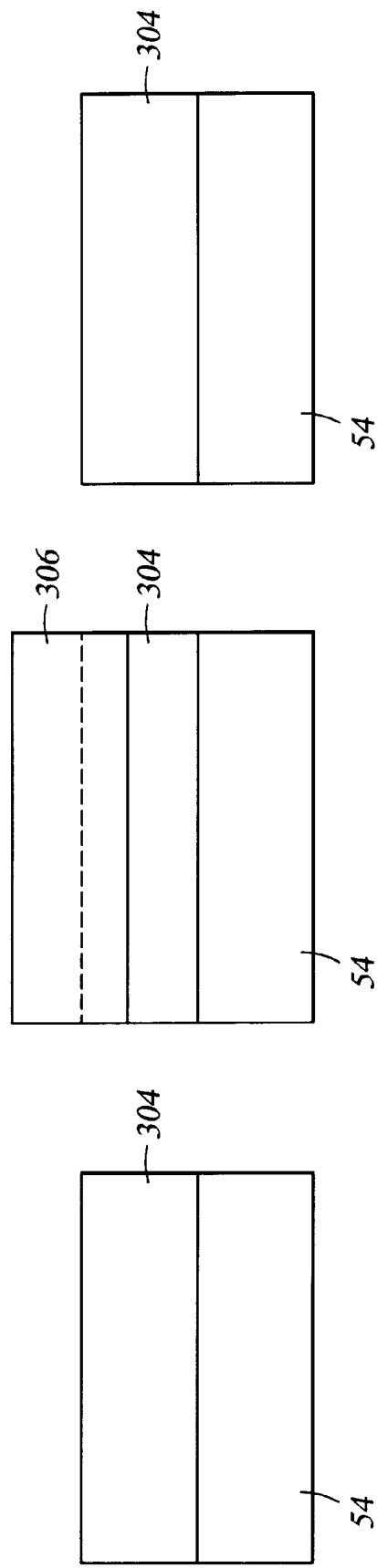
FIG. 3 is a schematic diagram illustrating oxide growth and removal on a substrate.

FIG. 3 schematically illustrates the substrate 54 having an at least partially exposed copper layer 304 such as a PVD seed layer that includes a film of copper native oxide 306 undergoing a reduction process. During the reduction reaction process, the hydrogen ions within the plasma react with the copper native oxide 306 to form metallic copper and water vapor as follows:

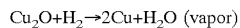

$Cu_2O+H_2 \rightarrow 2Cu+H_2O$ (vapor)

The chemical reaction reduces the copper native oxide 306 and leaves metallic copper where the copper native oxide previously occupied. Thus, no sputtering of the copper native oxide occurs during processing, and no unwanted copper native oxide is left within the interconnect feature.

Returning to FIG. 2, preferably after the desired processing time and the reduction of copper native oxide to copper, the power to the inductive coil 98 is continued, and the power supplied to the substrate support 42 is reduced to about 1 W. This step reduces particle generation as the reduction reaction period ends. Subsequently, the servo control throttle valve 94 is opened fully, and the powers supplied to the inductive coil 98 and substrate support 42 are turned off. The process gas flow over the substrate 54 is then increased to perform a final substrate surface conditioning step to reduce any static charges that may have built up during the process. After the final conditioning step, the processing gas supplied into the chamber 40 is shut off, and the chamber 40 is evacuated of the remaining processing gas and process by-products. The substrate 54 is then transferred out of the chamber 40 at step 106.

Figure 4:
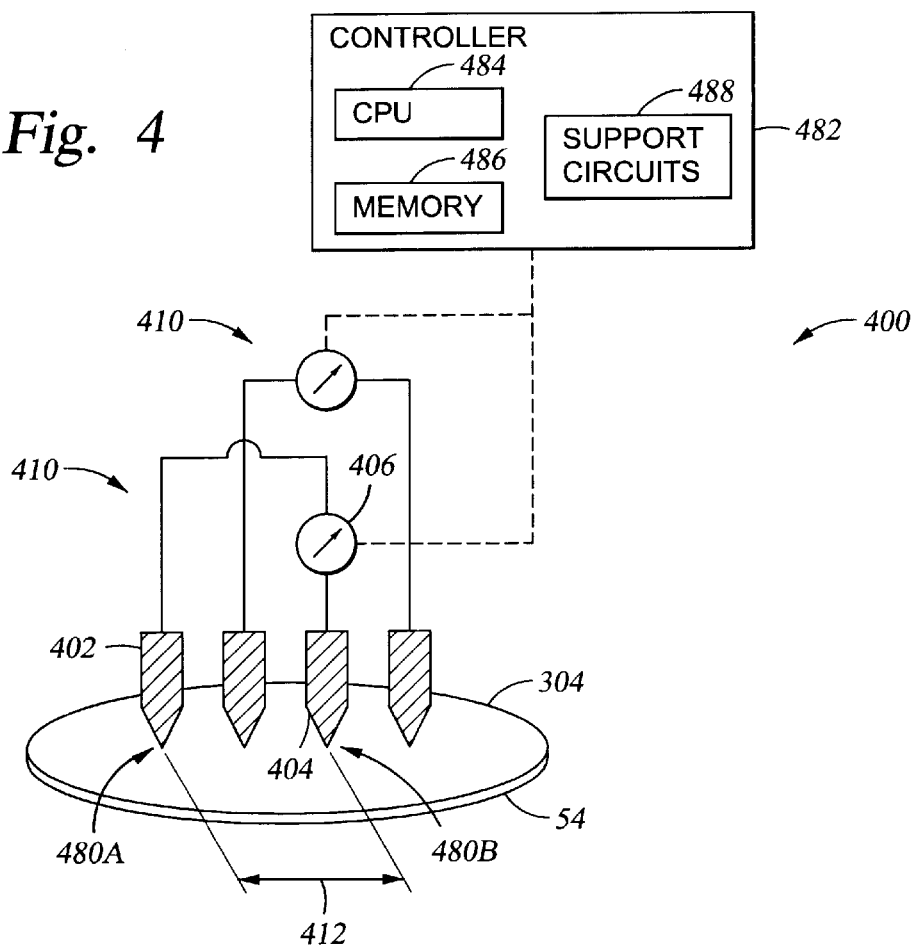
FIG. 4 is a schematic diagram illustrating one embodiment of a method of measuring the resistance of the exposed layer of the substrate.

FIG. 4 depicts a simplified schematic of one embodiment of a metrology device 400 that may be adapted to practice step 108 of the invention. Generally, the metrology device 400 includes one or more probe sets 410 that may be placed in contact with the exposed layer 306 of the substrate 54. In one embodiment, each probe set 410 includes a first contact pin 402, a second contact pin 404 and a resistance meter 406 coupled therebetween. The first and second contact pins 402, 404 are disposed in a predetermined spaced-apart relation 412. As the contact pins 402, 404 are placed in contact with the exposed layer 304, a points 480A and 480B on the substrate 54, the resistance across the known distance 412 of the layer 304 is determined. The measured resistance may be compared with known sheet resistance values for copper. By comparing the actual resistance value with the known sheet resistance for the material comprising the layer 304, the level of contamination (such as remaining native oxides 306) may be determined. Examples of metrology devices which may be adapted to benefit from the invention are available from EDTM, Inc, of Toledo, Ohio, Creative Design Engineering, and KLA-Tencor of San Jose, Calif. Using this information, the effectiveness of the pre-clean step 104 may be monitored.

In another embodiment, the probe sets 410 are coupled to a controller 482. The controller 482 generally includes a central processing unit (CPU) 484, support circuits 488 and memory 486. The CPU 484 may be one of any form of computer processor that can be used in an industrial setting for controlling various chambers and subprocessors. The memory 486 is coupled to the CPU 484. The memory 486, or computer-readable medium, may be one or more of readily available memory such as random access memory (RAM), read only memory (ROM), floppy disk, hard disk, or any other form of digital storage, local or remote and generally stores or has access to the known sheet resistance values. The support circuits 488 are coupled to the CPU 484 for supporting the processor in a conventional manner. These circuits include cache, power supplies, clock circuits, input/output circuitry, subsystems, and the like. The controller 482 may take the place of the meters 406 for each probe set 410.

Figure 5:
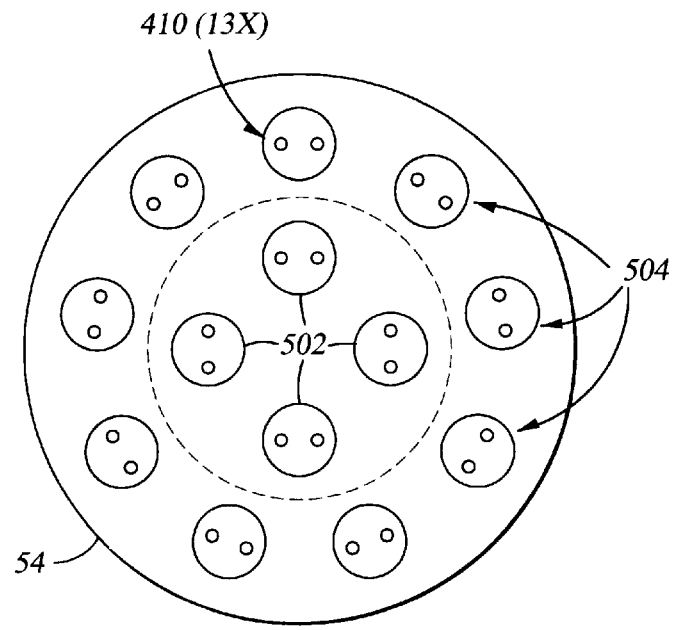
FIG. 5 is a schematic depicting one configuration of probes arranged to measure resistance on a substrate.

Generally, the controller 482 receives the resistance values obtained by the probe sets 410 and provides additional process information. For example, the probe sets 410 may be distributed across the substrate's surface and the resistance data may be used to provide an average sheet resistance. Alternatively, as depicted in FIG. 5, the probe sets 410 may be arranged in sub-groups, for example, a center group 502 and a perimeter group 504 disposed radially relative the center group 502, to determine the effectiveness of the process in one location relative another. The center and perimeter groups 502, 504 may each comprise one or more probe sets 410.

Figure 6:
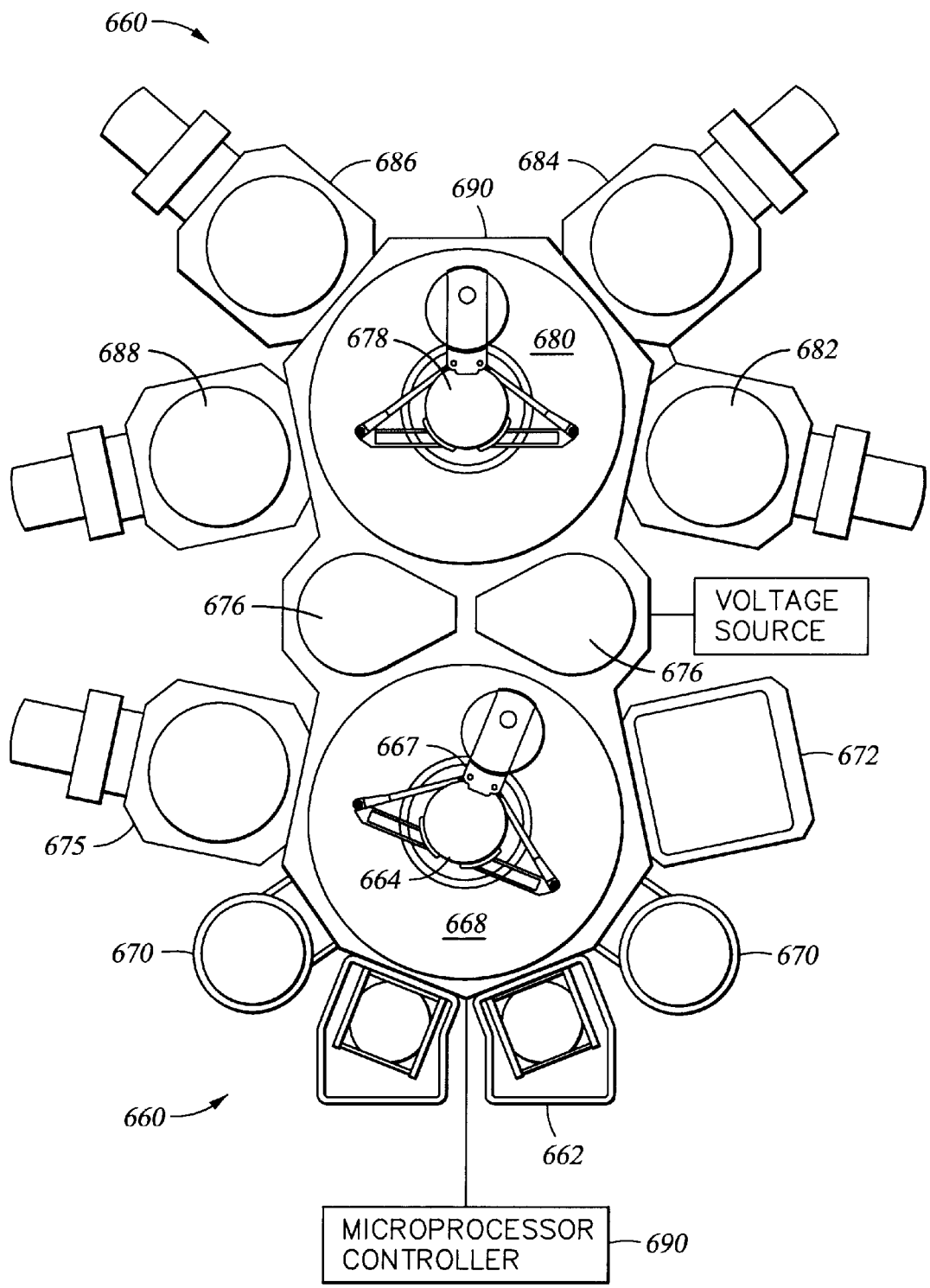
FIG. 6 is one embodiment of a processing system having a pre-clean chamber.

Referring to FIG. 6, a schematic diagram shows an integrated processing system 660 having a pre-clean chamber 672 for pre-cleaning of the substrates and both PVD and CVD chambers thereon in which integrated metallization processes can be implemented. The processing system 660 generally includes a transfer chamber 690 that is surrounded by a plurality of process chambers. Typically, the substrates are introduced and withdrawn from the processing system 660 through a cassette loadlock 662.

In one embodiment, the transfer chamber 690 includes a first buffer chamber 668 and a second buffer chamber 680. A first robot 664 having a blade 667 is located within the first buffer chamber 668. The first robot 664 transfers substrates between the cassette loadlock 662, degas wafer orientation chamber 670, remote plasma source pre-clean chamber 672, HP-PVD Ti/TiN chamber 675 and a cooldown chamber 676 which are disposed adjacent to the first buffer chamber 668. A second robot 678 is located in the second buffer chamber 680 and facilitates the transfer of substrates to and from the cooldown chambers 676, a PVD IMP Ti/TiN chamber 682, a CVD Al Chamber 684, a CVD TiN chamber 686, and a PVD HTHU Al chamber 688. Of course other process chambers may be substituted.

The second buffer chamber 680 in the integrated system is preferably maintained at low pressure or high vacuum in the range of $10^{-8}$ torr. The specific configuration of the chambers illustrated in FIG. 6 comprises an integrated processing system capable of both CVD and PVD processes in a single cluster tool. This particular chamber configuration or arrangement is merely illustrative and more configurations of PVD and CVD processes are contemplated by the present invention.

Generally, substrates are transferred between the first and second buffer chambers 668 and 680 through a cooldown chamber 676. Other transfer chambers 690 may be configured combining the buffer chambers 668 and 680 into a single chamber having a platform disposed therein to facilitate handoff of substrates between the robots 678 and 664, an examples of which is the ENDURA® SL processing platform, available from Applied Materials, Inc., Santa Clara, Calif.

Figure 7:
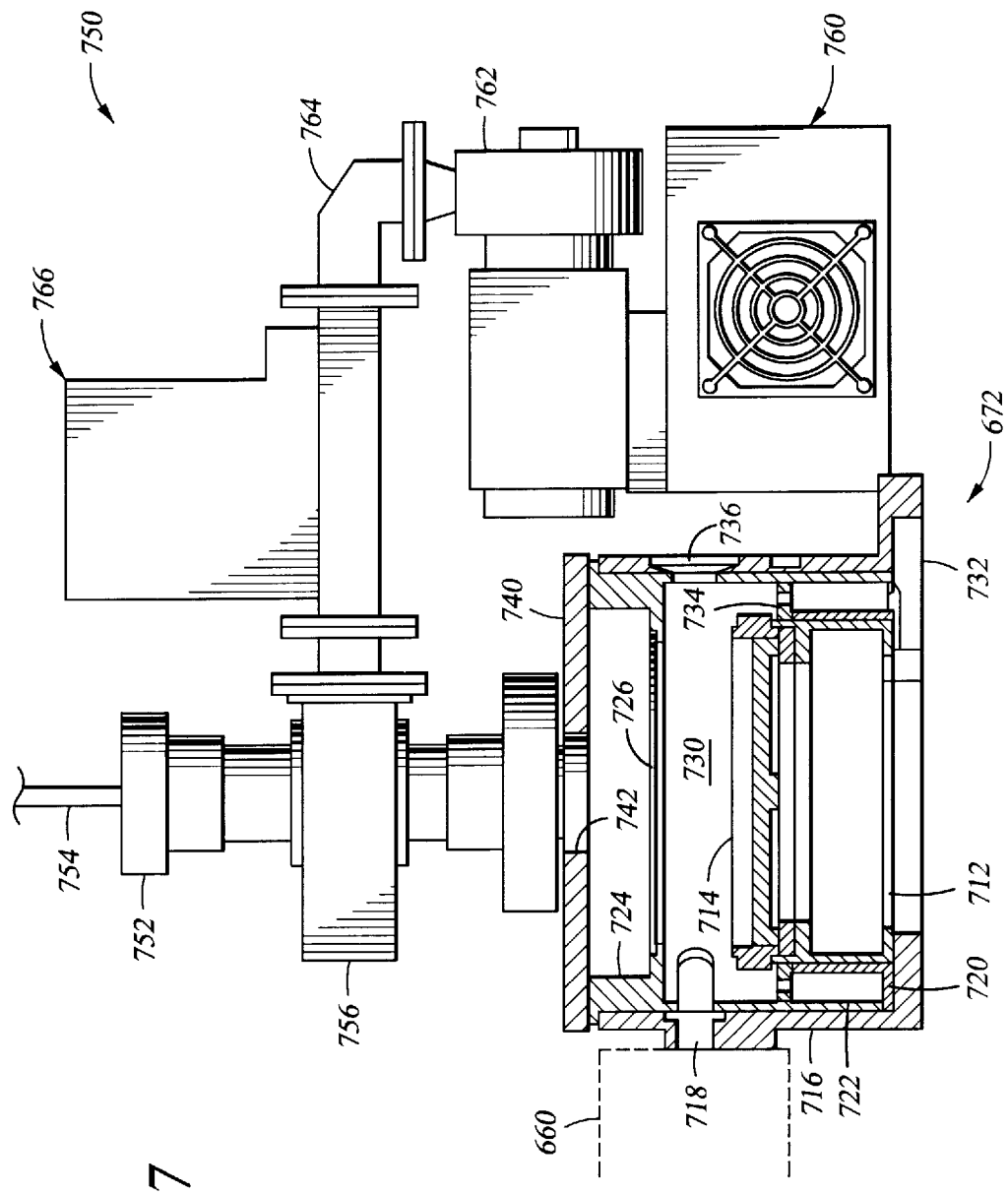
FIG. 7 is sectional view of another embodiment of a pre-clean chamber.

FIG. 7 depicts one embodiment of a pre-clean chamber 672. Generally, the pre-clean chamber 672 may be a remote plasma source (RPS) chamber such as the Etch RPS chamber which is also available from Applied Materials, Inc., of Santa Clara, Calif. Alternatively, a PRE-CLEAN™ II chamber as described above, or a metal CVD/PVD chamber having a remote plasma source coupled thereto among other chambers may be utilized. For example, gas inlets could be provided at the level of the substrate in the metallization chambers to deliver the reactive gas plasma or hydrogen plasma from the remote plasma source. Metal deposition chambers having gas delivery systems could be modified to deliver the pre-cleaning gas plasma through existing gas inlets such as a gas distribution showerhead positioned above the substrate.

The pre-clean chamber 672 generally includes two major assemblies: 1) a chamber body, including an electrostatic chuck which supports and secures a substrate in the chamber; and 2) a remote plasma source. These major assemblies will be discussed separately for the sake of organization, although it will be understood that in reality there is dynamic interaction between these assemblies. In a RPS chamber, reactive H radicals are formed and are primarily neutral species preventing generation of self bias and bombardment of the wafer surface by ions. Experiments with RPS chambers show that a 2.45 GHz microwave source is more efficient and can generate more hydrogen ions than lower frequency RF sources.

The pre-clean chamber 672 generally includes a chamber body 716 having a slit valve port 718 which connects the chamber 672 to the substrate processing system 660, such as an ENDURA® platform. A fixed cathode 712, which includes an electrostatic chuck 714 that secures the substrate (not shown) to the fixed cathode 712, is disposed within the chamber body 716.

The fixed cathode 712 is shielded from process gases by a cathode liner 720 that has a non-stick outer surface to enhance process performance. The chamber body 716 is also shielded from process gases by a chamber liner 722 which has a non-stick inner surface to enhance process performance. The chamber liner 722 includes an inner annular ledge 724 that supports a gas distribution plate 726. The gas distribution plate 726 has a plurality of spaced holes that distribute process gases over the surface of the substrate positioned on the electrostatic chuck 714.

A processing region 730 above the fixed cathode 712 is maintained at a low process pressure by vacuum pumps (not shown) which are in fluid communication with an exhaust port 732 on the chamber body 716. A baffle plate 734 having a plurality of spaced holes separates the processing region 730 from the exhaust port 732 to promote uniform exhausting around the fixed cathode 712. The processing region 730 is visible from outside the chamber 672 through a sapphire window 736 that is sealed in the chamber body 716.

The chamber body 716 has a removable chamber lid 740 that rests on the chamber liner 722. The chamber lid 740 has a central injection port 742 that receives process gases from the remote plasma source 750.

Process gases for the pre-cleaning process are excited into a plasma within the remote plasma source 750 which is in fluid communication with the chamber body 716 described above. A plasma applicator 752 has a gas inlet 754 that receives process gases. The process gases flow through the applicator 752 and exit into the central injection port 742 in the chamber lid 740. A jacket waveguide 756 surrounds a sapphire tube portion of the plasma applicator 752 and supplies microwave energy to the process gases.

Microwave energy is generated by a magnetron 760 that provides up to 1500 watts at 2.45 GHz. The microwave energy passes through a microwave isolator 762 that prevents reflected power from damaging the magnetron 760. The microwave energy from the isolator 762 is transmitted through a waveguide 764 to an autotuner 766 that automatically adjusts the impedance of the plasma in the applicator 752 to the impedance of the magnetron 760 thus resulting in minimum reflected power and maximum transfer of power to the plasma applicator 752.

In configurations where a metal CVD/PVD chamber having a remote plasma source coupled thereto is utilized, gas inlets typically are provided at the level of the substrate in the metallization chambers to deliver the reactive gas plasma or hydrogen plasma from the remote plasma source.

Metal deposition chambers having gas delivery systems could be modified to deliver the pre-cleaning gas plasma through existing gas inlets such as a gas distribution showerhead positioned above the substrate.

Returning to FIG. 6, the substrate is typically processed in the processing system 660 by transferring the substrate from the cassette loadlock 662 to the buffer chamber 668 where the robot 664 first moves the substrate into a degas chamber 670. After degas, the substrate is then transferred into the pre-clean chamber 672. After removal of native oxides and other contaminants, the substrate is transferred to the PVD HP TiN chamber 675 for barrier layer deposition, and then into a cooldown chamber 676. From the cooldown chamber 676, the robot 678 typically moves the substrate into and between one or more processing chambers before returning the substrate back to a cooldown chamber 676. It is anticipated that the substrate may be processed or cooled in one or more chambers any number of times in any order to fill the submicron features with aluminum or other materials. The substrate is removed from the processing system 660, following processing, through the buffer chamber 668 and then to the loadlock 662.

The processing system 660 passes a substrate through loadlock 662 into de-gas chamber 670 wherein the substrate is introduced to out gas contaminants. A substrate is then moved into the remote plasma source pre-clean chamber 672 where the submicron features are cleaned to remove any contaminants thereon and to reduce native oxides. The substrate is then processed in the PVD HP TiN chamber 675 to deposit a Ti/TiN barrier layer on the cleaned dielectric surfaces, and then passed to a cooldown chamber 676. The second robot 678 then transfers the substrate to one or more CVD and PVD chambers for deposition of aluminum, copper or other materials.

Another application of the integrated platform of FIG. 6 provides for copper deposition by providing a CVD TiN chamber 675, a PVD Cu chamber 682, a CVD Cu chamber 684, a PVD HTHU Cu chamber 686, and a PVD IMP Ta/TaN chamber 688. The substrate is processed in the CVD TiN chamber 675 or PVD IMP Ta/TaN chamber 688 to deposit a CVD TiN or Ta/TaN barrier layer on the cleaned dielectric surfaces, and then the substrate is passed to a cooldown chamber 676. Pre-cleaning of submicron features prior to copper deposition can be performed in the pre-clean chamber 672 or in a PRE-CLEAN™ chamber as described above which replaces a cooldown chamber 676. The second robot 678 then transfers the substrate to one or more CVD and PVD chambers for copper deposition. Deposited Cu layers may be annealed with $H_2$ to make the layer more resistant to formation of CuO.

Another application of the integrated platform 660 provides for tungsten deposition by providing a IMP Ti chamber, two CVD TiN chambers, and two pre-clean chambers. The substrate is processed in the IMP Ti and CVD TiN chambers to deposit Ti/TiN barrier layers on the cleaned dielectric surfaces, and then the substrate is passed to a cooldown chamber.

A staged-vacuum wafer processing method suitable for use with the present invention is disclosed in U.S. Pat. No. 5,186,718, entitled Staged-Vacuum Wafer Processing System and Method, issued Feb. 16, 1993 to Tepman et al., and is hereby incorporated herein by reference. This method readily accommodates the pre-cleaning method of this invention. Any combination of processing chambers can be used with the dedicated pre-cleaning chamber.

While the foregoing is directed to the preferred embodiment of the present invention, other and further embodiments of the invention may be devised without departing from the basic scope thereof. For example, native oxides and other contaminants may be removed from layers other than copper. The scope of the invention is determined by the claims that follow.

What is claimed is:

1. A method for monitoring a process of removing native oxides from an at least partially exposed layer disposed on a substrate, the method comprising:

disposing the substrate in a process chamber;

exposing the at least partially exposed layer to a reactive pre-clean process;

removing the substrate from the process chamber; and measuring a sheet resistance of the exposed layer.

2. The method of claim 1, wherein the step of measuring the sheet resistance further comprises:

contacting the at least partially exposed layer with at least one probe set, the probe set comprising two or more contact members coupled to a resistance meter.

3. The method of claim 1, wherein the step of measuring the sheet resistance further comprises:

contacting the at least partially exposed layer with a plurality of probe sets, each probe set comprising two or more contact members disposed in a spaced-apart relation.

4. The method of claim 3, wherein the step of contacting the exposed layer further comprises:

contacting the exposed layer with a first group of probe sets; and contacting the exposed layer with a second group of probe sets disposed radially outward from the first group of probe sets.

5. The method of claim 3, wherein the step of measuring the sheet resistance further comprises:

comparing the measured resistance between the first and second groups of probe sets.

6. The method of claim 3, wherein the step of measuring the sheet resistance further comprises:

averaging the measured resistance.

7. The method of claim 1 further comprising:

comparing the measured sheet resistance to a sheet resistance known for the at least partially exposed layer.

8. The method of claim 1, wherein the reactive pre-clean process comprises:

forming a plasma from a gas comprising an inert carrier gas combined with less than about 5 percent hydrogen; and reducing native copper oxide from the at least partially exposed layer.

9. The method of claim 8, wherein the reactive pre-clean process further comprises:

inductively coupling about 1 to about 1000 Watts to the plasma; and biasing a substrate support with less than about 100 Watts.

10. A method for monitoring a process of removing native oxides from an at least partially exposed conductive layer disposed on a substrate, the method comprising:

disposing the substrate in a process chamber;

exposing the at least partially exposed conductive layer to a reactive pre-clean process that comprises an oxide reduction step;

removing the substrate from the process chamber;

contacting the conductive layer with two or more contact members;

measuring a sheet resistance of the exposed conductive layer between the contact members; and comparing the measured resistance to a known value.

11. The method of claim 10, wherein the step of contacting the at least partially exposed conductive layer further comprises:

contacting the exposed conductive layer with at least one probe set, the probe set comprising two or more contact members coupled to a resistance meter.

12. The method of claim 10, wherein the step of contacting the exposed layer further comprises:

contacting the exposed conductive layer with a first group of probe sets; and contacting the exposed conductive layer with a second group of probe sets disposed radially outward from the first probe set.

13. The method of claim 10, wherein the step of measuring the sheet resistance further comprises:

comparing the measured resistance between the first and second groups of probe sets.

14. The method of claim 10, wherein the step of measuring the sheet resistance further comprises:

averaging the measured resistance.

15. The method of claim 10, wherein the reactive pre-clean process comprises:

forming a plasma from a gas comprising an inert carrier gas combined with less than about 5 percent hydrogen; and reducing native copper oxide from the exposed conductive layer.

16. The method of claim 15, wherein the reactive pre-clean process comprises:

inductively coupling about 1 to about 1000 Watts to the plasma; and biasing the substrate support with less than about 100 Watts.

17. The method of claim 10, wherein the conductive layer is aluminum or copper.

18. A method for monitoring a process of removing native copper oxide from an at least partially exposed copper layer disposed on a substrate, the method comprising:

disposing the substrate in a process chamber;

exposing the at least partially exposed copper layer to a reactive pre-clean process that comprises exposing the copper oxide to a plasma formed from a hydrogen comprising gas;

removing the substrate from the process chamber;

contacting the exposed copper layer with two or more contact members;

measuring a sheet resistance of the exposed copper layer between the contact members; and comparing the measured resistance to a known value.

19. A method for monitoring a process of removing native oxides from an at least partially exposed conductive layer disposed on a substrate, the method comprising:

exposing the exposed conductive layers to a plasma at least partially formed from hydrogen in a first chamber coupled to a processing platform to remove native oxides from the exposed conductive layer;

transferring at least one of a series of substrates exposed to the plasma from the first chamber to a metrology device;

measuring the sheet resistance of the conductive layer; and comparing the measured sheet resistance to a known value.

20. The method of claim 19, wherein the measured substrate is one of a series of production substrates being processed.

21. The method of claim 19, wherein the measured substrate is a utility substrate.

22. The method of claim 19, wherein the step of measuring the sheet resistance further comprises:

contacting the exposed layer with at least one probe set, the probe set comprising two or more contact members coupled to a resistance meter.

23. The method of claim 22, wherein the step of contacting the exposed layer further comprises:

contacting the exposed layer with a first group of probe sets; and contacting the exposed layer with a second group of probe sets disposed radially outward from the first probe set.

24. The method of claim 19, wherein the step of measuring the sheet resistance further comprises:

comparing the measured resistance between the first and second groups of probe sets.

25. The method of claim 19, wherein the step of measuring the sheet resistance further comprises:

averaging the measured resistance.

26. The method of claim 19, wherein the reactive pre-clean process comprises:

forming a plasma from a gas comprising an inert carrier gas combined with less than about 5 percent hydrogen; and reducing native copper oxide from the exposed layer.

27. The method of claim 26, wherein the reactive pre-clean process comprises:

inductively coupling about 1 to about 1000 Watts to the plasma; and biasing a substrate support with less than about 100 Watts.

28. A method for processing a substrate, comprising:

removing oxides from an at least partially exposed layer disposed on the substrate in a first chamber;

measuring a sheet resistance of the exposed layer; and depositing a conductive layer on the substrate in a second chamber, wherein the substrate is transferred between the chambers without breaking vacuum.

29. The method of claim 1, wherein removing oxides comprises:

forming a plasma from a gas comprising an inert carrier gas combined with less than about 5 percent hydrogen; and reducing the oxides from the at least partially exposed layer.

30. A method for processing a substrate, comprising:

removing oxides from an at least partially exposed layer disposed on the substrate in a first chamber;

measuring a sheet resistance of the exposed layer in a second chamber; and depositing a conductive layer on the substrate in a third chamber, wherein the substrate is transferred between the chambers without breaking vacuum.

31. A method for processing a substrate, comprising:

providing a substrate having a copper layer at least partially disposed on a surface thereof in a first chamber;

removing native oxides from the copper layer in the first chamber;

measuring a sheet resistance of the copper layer;

depositing a barrier layer at least partially on the substrate surface in a second chamber; and depositing a bulk metal layer at least partially on the substrate surface in a third chamber, wherein the substrate is transferred between at least the first and second chambers without breaking vacuum.

* * * * *